United States Patent [19]

Erickson

[11] Patent Number: 4,925,305

[45] Date of Patent: May 15, 1990

[54] METHOD FOR THE PRESERVATION OF WHEAT AND DEVICE USEFUL THEREFORE

[76] Inventor: Ronald R. Erickson, 167 Garfield Pl., Brooklyn, N.Y. 11215

[21] Appl. No.: 278,564

[22] Filed: Dec. 1, 1988

[51] Int. Cl.$^5$ .......................... G01J 3/00; G01N 21/35
[52] U.S. Cl. ..................................... 356/300; 250/339; 250/341; 250/252.1; 356/243
[58] Field of Search .............. 356/319, 326, 328, 331, 356/334, 243, 300; 350/3.7; 250/252.1 A, 339, 341

[56] References Cited

U.S. PATENT DOCUMENTS 4,087,183  5/1978  Passereau ........................ 350/3.7
4,571,074  2/1986  Thevenon ......................... 356/328

FOREIGN PATENT DOCUMENTS

167750  1/1986  European Pat. Off. ............ 356/328

Primary Examiner—F. L. Evans
Attorney, Agent, or Firm—Handal & Morofsky

[57] ABSTRACT

A humidity measuring device and standard is disclosed. Humidity is measured by comparing the reflectivity and selected wavelengths of light of a grain sample to the reflectivity of a standard of known humidity in order to ascertain humidity. A holographically generated reflecting standard with a sculptured wavelength and amplitude filtering element is utilized.

17 Claims, 6 Drawing Sheets

METHOD FOR THE PRESERVATION OF WHEAT AND DEVICE USEFUL THEREFORE

TECHNICAL FIELD

The present invention relates to an improved method for measuring the moisture content of wheat whereby the same may be regulated to optimize maintenance of the nutritional value of the grain.

BACKGROUND

Long before the dawn of recorded history, man has cultivated various plants for the nutritional value of their fruits and grains. The majority of important food plants today have originated from three principle regions of the world, namely, the fertile crescents in the Middle East, the southern Chang Jian River valley and Yunnan Province in China, and the relatively arid areas in the foothills of the Andres Mountains in Peru. These areas, while separated by great geographic distances, share one important characteristic, which, in the evolutionary history of plant life on earth, have caused the plants of those areas to develop fruits with relatively large volumes of highly nutritional substances.

In particular, relatively long arid periods in each area cause native plants to evolve survival strategies centering around highly efficient systems for the storage of moisture and nutrition to sustain the development of new plants. Specifically, these systems took the form of large seeds (such as wheat), fruits (such as tomatoes), tubers (such as potatoes) and bulbous root systems (such as onions). Even today, agricultural scientists concentrate their efforts for gathering new genetic breeding materials on these areas of the earth due to the great variety of plants available, only a tiny fraction of which have been commercially developed.

Just about as soon as human populations began the cultivation of food plants, storage and preservation of the same became a primary problem for solution. Food products that cam e from the grasses offered especially promising opportunities in this regard. To those early farmers, grains such as barley, rye, alba and corn must have seemed to have almost unlimited useful shelf life. Thus, Aztec corn and Greek alba both found their way into granaries which were invented in similar fashion on both sides of the Atlantic Ocean. Generally, these storage facilities, which remain unchanged in their essentials since ancient times, are large closed spaces which protect the grain from the adverse environment effects of rain and sun. While the ancients could hardly have suspected the effects of long term exposure to ultra-violet radiation on nutritive value, the more obvious connection between excess moisture and rot suggested keeping grain in closed receptacles, a solution which simultaneously addressed many of the problems associated with other aspects of the deterioration of grains, including ultra-violet deterioration.

One of the most important events in the agricultural history of western man was the discovery, probably in a field of alba, of a particular plant which would come to be known as wheat. An incidental but most important characteristic of this plant was the fact that when a number of grains were rubbed against each other, the coarse shell of the seed, also known as the chaff, would fracture and become disassociated from the kernel. This mutation eventually came to supplant alba almost in its entirety.

As man's use of wheat continued to grow, he came to learn about the preservation of the wheat and the pernicious effects of moisture and dryness. In particular, if wheat was allowed to become too moist, it rotted. On the other hand, if wheat become too dry, it lost flavor and, as learned relatively recently, it also lost nutritional value. Thus, it has long been an object in wheat storage to maintain the maximum possible moisture without encouraging fungal degradation of the grain.

It also came to be learned that the best way of judging the moisture content of the wheat is by the color of the grain. Thus a skilled granger periodically checks wheat from various parts of the granary and observes the color thereof from which he can judge the moisture content of the grain. In recent years, higher moisture contents can be maintained by, for example, fumigation of the grain with anti-fungal agents. In addition, while economically impractical, grain moisture content can be maintained at a high level by refrigeration of the grain.

More recently, less precise methods of visual observation of grain color have been replace by the measurement of grain color using optical instrumentation. Such instruments as spectrum analyzers compare light from a standard sample of grain of known humidity which is hermetically housed behind a sodium chloride window. Light reflected by an unknown sample is analyzed and the spectral content of the reflected light is compared to the reflected by standards of known humidity to find a match, thus indicating that the unknown has the same humidity as the known matched standard sample.

Unfortunately, such standard samples are very expensive to manufacture and have extremely limited life. Accordingly, they must be constantly replaced at great cost. The present invention has the object of dispensing with this difficulty.

SUMMARY OF THE INVENTION

In accordance with the present invention, the controlled humidity sample grain standard of the prior art is replaced with a sculpture controlled dyeless optical filtration device which may be directly substituted for known humidity grain standards in black body integrating sphere spectroanalysis systems of the type presently being used in the field. Because of the dyeless and inorganic nature of the standard, individual inventive standards have indefinite durability. Replication of standards is considerably less expensive than in the case of existing real grain standards. Moreover, accuracy is far easier to control and improved results may be obtained.

BRIEF DESCRIPTION OF THE DRAWINGS

One way of carrying out the invention is described in detail below with reference to drawings which illustrate only one specific embodiment of the invention and in which.

BEST MODE FOR CARRYING OUT THE INVENTION

Figure 1:
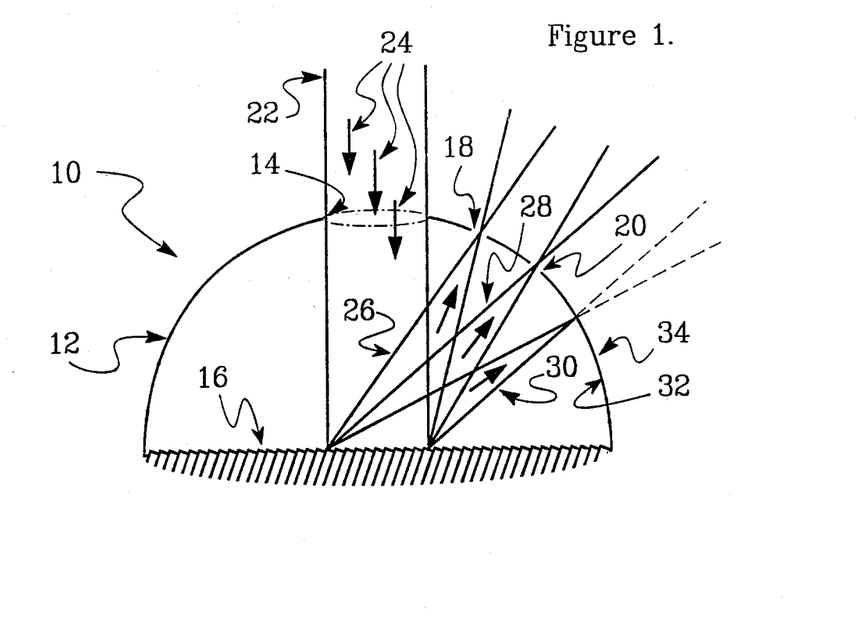
FIG. 1 is a is a schematic view of a reflectivity standard constructed in accordance with the present invention.

Referring to FIG. 1, a humidity standard 10 constructed in accordance with the present invention is illustrated. Standard 10 generally comprises a housing 12 having an input light port 14, a diffracting surface 16 and a plurality of output ports 18 and 20.

The principle of operation is that an incoming wide band infrared beam 22 containing different wavelengths of light 24 passes through input 14 striking the surface of diffractor 16. This causes the light to break down into component light beams of different wavelengths such as beams 26, 28, and 30. In practice, most sources would give a large number of wavelengths and only three wavelengths are illustrated in the drawing for simplicity of illustration. The effect of the sculptural shape of housing 12 and the position of outlet ports or slits 18 and 20 is to pass output beams 26 and 28 while causing the blocking of output beam 10. Thus analysis is limited to particular wavelengths of interest.

It is noted that both the inside surface 32 and the outside surface 34 are coated black. This blocks wavelengths of light such as those of beam 30, which are absorbed by the black inside surface 32. Likewise, stray radiation will be absorbed by the black coating on the outside surface 34 of housing 12. Of course, the blackening of the outside surface 34 is far less critical than the blackening of inside surface 32 and if a high degree of accuracy is not required may even be dispensed with.

It is contemplated that diffractor 16 will be a diffraction grating preferably having focusing characteristics. Accordingly, while the ruling of such a grating is possible using a mechanical ruling engine (for example, one may rule a conventional Rowland grating and place exit slits 18 and 20 along the appropriate Rowland Circle), it is contemplated that the subject grating would be replicated from a holographic master.

Such holographic masters, like their mechanically ruled counterparts, are easily replicated by impressing a replica of the master grating into a cellulose acetate butyrate blank or other known techniques. Replicated grating grooves would then be over-coated with gold for high reflectivity in the infrared region as well as a high degree of environmental stability.

As alluded to above, it is contemplated that the use of holographically fabricated gratings would be preferable to using mechanically ruled devices. In particular, holographically generated gratings, such as grating 216, in FIG. 2 which may have a plurality of grating structures (not evident in a sectional view), have the advantage of providing a self-focusing function without the addition of the optical elements such as mirrors and lenses and, for example, may even provide a spectrum which is planar in configuration. Obviously, this allows for easy fabrication of a housing 212 to include a planar sculptured filtering surface 236 incorporating an inlet slit 214 and outlet slits 238, 240 and 242 which are positioned to pass light beams 244, 246 and 248 of different wavelengths. The position of the outlet slits controls the wavelength passed and the width of the slit controls the amplitude at that wavelength. Such self-focusing diffraction gratings which provide planar spectra are available from Instruments SA, Inc. of Edison, N.J.

Figure 2:
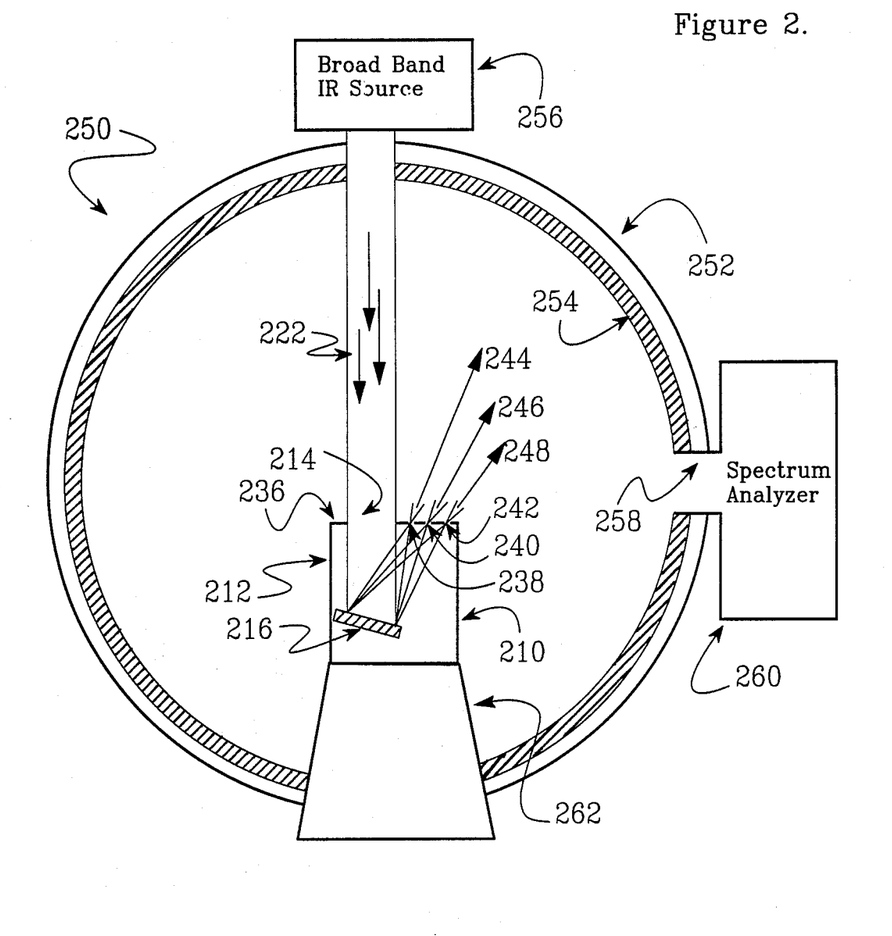
FIG. 2 is a view of a system incorporating the inventive humidity standard.

As noted above, the position of the slit along the focal plane determines the wavelength of the light emitted from the housing. The wavelength transition, or precision of tuning in on a particular wavelength to the exclusion of adjacent wavelengths, may be determined by the amount of displacement of the slit from the focal plane. Therefore slit size and placement determines the wavelength, the wavelength transition and the amplitude of the light emitted from the housing.

The holographic grating has another advantage over the mechanically ruled gratings in that it is capable of capturing different grating structures. Gratings may be superimposed with different axis orientation. In this way three grating structures may be superimposed and oriented at 120° with respect to each other.

A housing associated with a triple grating structure would then be fashioned with three sets of slits. This allows for the custom construction of the desired standard spectrum as shown in FIGS. 3 and 4.

Figure 3A:
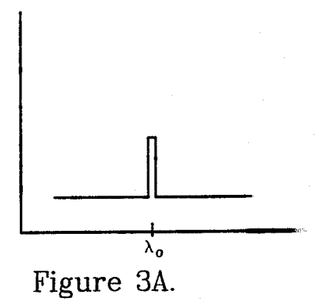
FIGS. 3A to 3C are individual spectra generated in the neighborhood of wavelength $\lambda_0$.
Figure 3B:
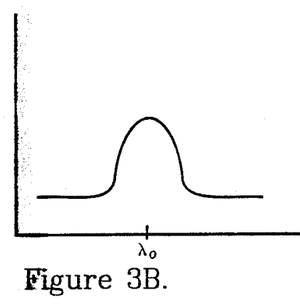
Figure 3C:
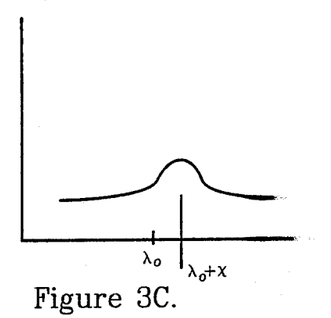
Figure 3D:
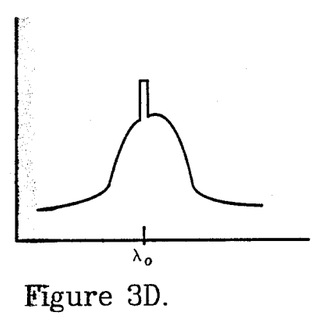
FIG. 3D is a composite spectrum encompassing FIGS. 3A to 3C.

The triple grating structure system may build a composite spectrum in the area of wavelength $\lambda_0$ in the following manner. The triple grating will have three associated focal planes each with a corresponding wavelength $\lambda_n$. One slit of width W is positioned at $\lambda_0$ on one focal plane giving a spectrum as shown in FIG. 3A. A second slit is positioned at $\lambda_0$ but displaced from a second focal plane giving the less sharp (hump vs spike) spectrum as shown in FIG. 3B. A third slit associated with the remaining focal plane is of a small width, positioned at $\lambda_0+x$ and removed from the focal plane giving the spectrum of FIG. 3C. The system as a whole will then produce a composite spectrum as in FIG. 3D for the area of $\lambda_0$, showing an asymmetrical area around $\lambda_0$ with a spike at $\lambda_0$.

Figure 4:
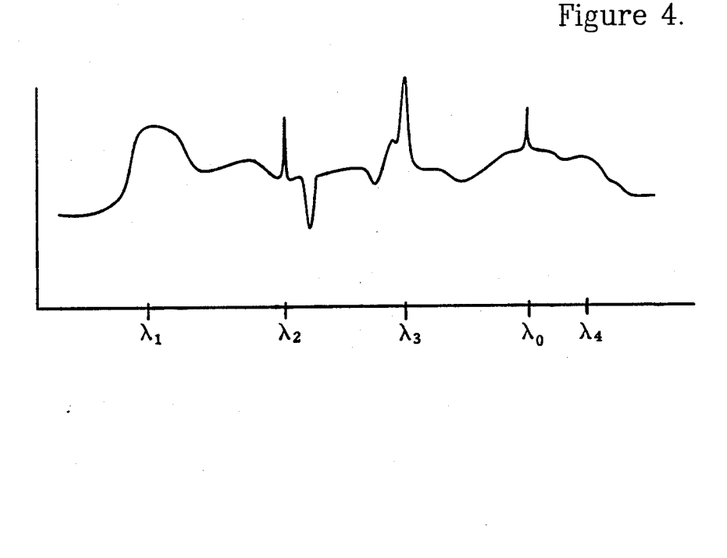
FIG. 4 shows a spectrum combining several composite spectra of different wavelength ranges.
Figure 5A:
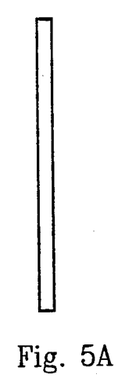
FIG. 5 shows a variety of slit shapes that may be utilized in the instruction of a desired spectrum.
Figure 5B:
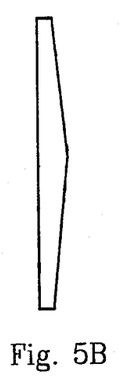
Figure 5C:
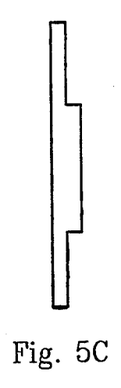
Figure 5D:
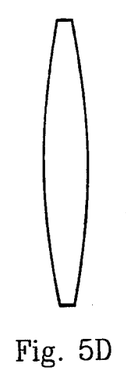
Figure 5E:
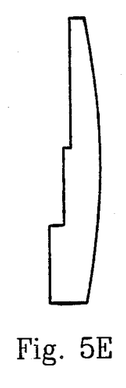

By the use of several slits with each of the three focal planes, composite spectrums for the neighborhoods of several different wavelengths will combine to give a spectrum such as that in FIG. 4. Through proper placement of the slits a spectrum may be constructed conforming to desired characteristics.

A variety of slit shapes, as illustrated in FIG. 5, may also be employed in fine tuning the emitted spectrum to more closely resemble the desired spectrum. Thus a spectrum may be fixed and available representing perishable or ephemeral samples not always available and often quite expensive.

Figure 6:
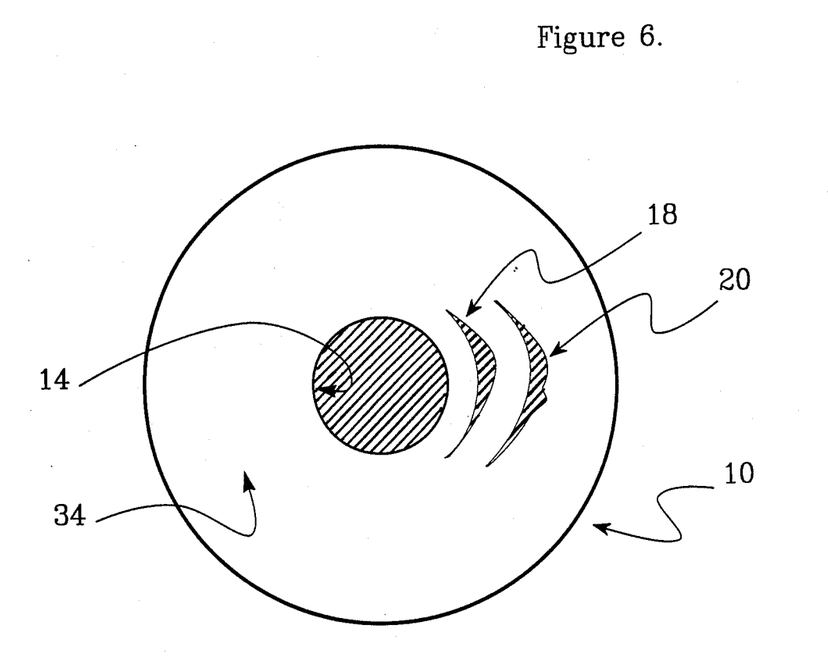
FIG. 6 is a top schematic view of a reflectivity standard as shown in FIG. 1.

FIG. 6 is a top view of the humidity standard 10 of FIG. 1. Here it may be seen that slits 18 and 20 may be of irregular shape in order to allow passage of the desired wavelenghts. FIG. 6 contemplates a domed housing. Such a shaped housing may require different shaped slits than a rectalinear housing, such as the one illustrated in FIG. 2, to produce a similar standard spectrum.

A spectral analysis system 250 with which a humidity standard 210 constructed in accordance with the present invention may be used, is illustrated in FIG. 2. Generally, the analyzer 250 comprises an outer housing 252 which contains an inside silvered surface 254 which acts to internally reflect and thus integrate exiting light beams 244, 246 and 248 reflected by grating 216 in response to input broadband infrared light beam 222 which is output by broadband IR source 256. The output of the integrator is received through port 258 which is coupled to a spectrum analyzer 260. The standard for a sample of grain to be analyzed is supported on platform 262.

When it is decided to use the inventive system, a humidity standard 210 having the light reflective characteristics for certain selected wavelengths of light which are identical to the characteristics of a sample of grain of known humidity is place on platform 262 and a reading taken with spectrum analyzer 260. A sample is then placed on platform 262 and another reading with the spectrum analyzer 260 is taken. One then compares the readings with the standard and the sample and if a match occurs, the humidity of the sample of grain is known to be that of the standard. If not, another standard is inserted into the machine and the reading compared until a standard is found which substantially matches the readings obtained with the sample.

With computer technology the standards may be analyzed and used for calibration of the system to allow the humidity of a sample to be determined immediately through interpolation.

Variability of the light source and detector can both contribute to the need to periodically recalibrate and standardize the instruments.

While an illustrative embodiment of the invention has been described, it is of course understood that various modifications will be obvious to those of ordinary skill in the art. Such changes and modifications are within the scope of the invention which is limited and defined only by the appended claims.

I claim:
1. A humidity standard, comprising:
  (a) a housing;
  (b) a diffracting surface contained within said housing;
  (c) an input port defined by said housing; and
  (d) a plurality of output ports defined in said housing, said output ports being positioned with respect to said input port and said diffracting surface to allow light of wavelengths corresponding to the wavelengths of light reflected by a sample substance of known humidity, to pass, with respective intensities proportional to the amplitude of light of the respective wavelength as would be reflected by said sample substance.

2. A humidity standard as in claim 1, wherein said outlet ports have an area proportional to the amplitude of light of the respective wavelength which one wishes to pass.

3. A humidity standard as in claim 1, wherein said diffracting surface is a holographically fabricated grating.

4. A humidity standard as in claim 3, wherein said holographically fabricated grating is self-focusing.

5. A humidity standard as in claim 3, wherein said holographically fabricated grating contains a plurality of self-focusing grating structures, said structures having different axis orientation.

6. A humidity standard as in claim 4, wherein the housing is proportioned and dimensioned such that the output ports are positioned with respect to a focal plane associated with said self-focusing grating to give the wavelength transition required.

7. A humidity standard as in claim 1, wherein said housing has an interior surface that is blackened to prevent reflection and scattering of the light not selected to pass through said output ports.

8. Apparatus for measuring humidity content of a sample of grain, comprising:
  (a) a humidity standard, comprising:
    (i) a housing;
    (ii) a diffracting surface contained within said housing;
    (iii) an input port defined by said housing; and
    (iv) a plurality of output ports defined in said housing, said output ports beings positioned with respect to said input port and said diffracting surface to allow light of certain wavelengths to pass;
  (b) a closed body with an internal reflective surface, said internal surface defining a chamber containing said standard;
  (c) a light input port defined by said closed body;
  (d) a light output port defined by said closed body;
  (e) a broadband light source coupled to said input light port to send light to said input port of said standard; and
  (f) a spectral analyzer coupled to said output light port to receive light passing through said output ports of said standard and reflected by said internal surface.

9. Apparatus as in claim 8, wherein said outlet ports of the humidity standard have an area proportional to the amplitude of light of the respective wavelengths which one wishes to pass.

10. Apparatus as in claim 8, wherein said diffracting surface is a holographically fabricated grating.

11. Apparatus as in claim 10, wherein said holographically fabricated grating is self-focusing.

12. Apparatus as in claim 10, wherein said holographically fabricated grating contains a plurality of self-focusing grating structures, said structures having different axis orientation.

13. Apparatus in claim 11, wherein the housing is proportioned and dimensioned such that the output ports are positioned with respect to a focal plane associated with said self-focusing grating to give the wavelength transition required.

14. Apparatus in claim 8, wherein said housing has an interior surface that is blackened to prevent reflection and scattering of the light not selected to pass through said output ports.

15. Apparatus in claim 13, wherein said wavelengths and amplitudes received by said spectral analyzer correspond to indicative wavelengths, and their corresponding amplitudes emitted by a sample of grain of known humidity.

16. A method of determining the humidity of a sample of grain using a system comprising:
  (a) at least one humidity standard, comprising:
    (i) a housing;
    (ii) a diffracting surface contained within said housing;
    (iii) an input port defined by said housing; and
    (iv) a plurality of output ports defined in said housing, said output ports being positioned with respect to said input port and said diffracting surface to allow light of certain selected indicative wavelengths to pass;
  (b) a closed body with an internal reflective surface, said internal surface defining a chamber containing said standard;
  (c) a light input port defined by said closed body;
  (d) a light output port defined by said closed body;
  (e) a broadband light source coupled to said input light port to send light to said input port of said standard; and
  (f) a spectral analyzer coupled to said output light port to receive light passing through said output ports of said standard and reflected by said internal surface, said method comprising the steps of:

(I) measuring the amplitude of said indicative wavelengths with a sample of grain in said closed body;

(II) measuring the amplitude of said indicative wavelengths of a humidity standard;

(III) comparing the measurement of step II with that of step one; and if the measurements do not match (IV) repeating steps (II) and (III) with one or more standards until a match is substantially made between the sample and a standard.

17. A method of determining the humidity of a sample of grain using a system comprising:

(a) a plurality of humidity standards, each comprising:

(i) a housing;

(ii) a diffracting surface contained within said housing;

(iii) an input port defined by said housing; and (iv) a plurality of output ports defined in said housing, said output ports being positioned with respect to said input port and said diffracting surface to allow light of certain selected indicative wavelengths to pass;

(b) a closed body with an internal reflective surface, said internal surface defining a chamber containing said standard;

(c) a light input port defined by said closed body;

(d) a light output port defined by said closed body;

(e) a broadband light source coupled to said input light port to send light to said input port of said standard; and (f) a spectral analyzer coupled to said output light port to receive light passing through said output ports of said standard and reflected by said internal surface, said method comprising the steps of:

(I) measuring the amplitude of said indicative wavelengths of a range of humidity standards in order to calibrate said spectral analyzer;

(II) measuring the amplitude of said indicative wavelengths with a sample of grain in said closed body; and (III) comparing the values measured with said sample to the calibration measurements of said humidity standards and arriving at a humidity value of said sample through interpolation.

* * * * *